United States Patent
Richeson et al.

(10) Patent No.: US 9,279,047 B2
(45) Date of Patent: *Mar. 8, 2016

(54) POLYMER COMPOSITIONS AND NONWOVEN COMPOSITIONS PREPARED THEREFROM

(71) Applicant: ExxonMobil Chemical Patents Inc., Baytown, TX (US)

(72) Inventors: Galen C. Richeson, Humble, TX (US); Rainer Kolb, Kingwood, TX (US); Jean-Roch H. Schauder, Wavre (BE); Thomas T. Sun, Clinton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/202,869

(22) Filed: Mar. 10, 2014

(65) Prior Publication Data

US 2014/0194845 A1    Jul. 10, 2014

Related U.S. Application Data

(62) Division of application No. 13/310,146, filed on Dec. 2, 2011, now Pat. No. 8,710,148.

(51) Int. Cl.
| | |
|---|---|
| *C08L 23/14* | (2006.01) |
| *C08L 23/10* | (2006.01) |
| *C08F 210/06* | (2006.01) |
| *A61L 15/26* | (2006.01) |
| *D04H 3/007* | (2012.01) |
| *D04H 3/16* | (2006.01) |
| *C08F 4/659* | (2006.01) |
| *C08F 4/6592* | (2006.01) |

(52) U.S. Cl.
CPC ............... *C08L 23/14* (2013.01); *A61L 15/26* (2013.01); *C08F 210/06* (2013.01); *C08L 23/10* (2013.01); *D04H 3/007* (2013.01); *D04H 3/16* (2013.01); *C08F 4/65908* (2013.01); *C08F 4/65927* (2013.01)

(58) Field of Classification Search
CPC ............... C08F 210/06; C08F 4/65927; C08F 4/65908; D04H 3/16; D04H 3/007; C08L 23/14; C08L 23/10; C08L 2308/00; C08L 2205/025; A61L 23/142
USPC ............ 525/191, 240; 604/372; 442/328
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,340,563 A | 7/1982 | Appel et al. | |
| 4,540,753 A | 9/1985 | Cozewith et al. | |
| 6,248,833 B1 | 6/2001 | Colucci et al. | |
| 6,268,302 B1 | 7/2001 | Ofosu et al. | |
| 6,440,882 B1 | 8/2002 | Colucci et al. | |
| 6,525,157 B2 | 2/2003 | Cozewith et al. | |
| 6,881,800 B2 | 4/2005 | Friedersdorf | |
| 7,601,666 B2 | 10/2009 | Rix et al. | |
| 7,619,038 B2 | 11/2009 | Mehta et al. | |
| 2002/0019507 A1 | 2/2002 | Karandinos et al. | |
| 2004/0236042 A1 | 11/2004 | Datta et al. | |
| 2005/0130544 A1* | 6/2005 | Cheng et al. | ................ 442/415 |
| 2008/0172840 A1 | 7/2008 | Kacker et al. | |
| 2009/0124154 A1 | 5/2009 | Harrington et al. | |
| 2009/0149605 A1 | 6/2009 | Li et al. | |
| 2009/0311938 A1 | 12/2009 | Campbell et al. | |
| 2010/0152388 A1 | 6/2010 | Jiang et al. | |
| 2012/0123374 A1* | 5/2012 | Richeson et al. | ............ 604/372 |
| 2012/0329351 A1* | 12/2012 | Mehta et al. | ................ 442/328 |

FOREIGN PATENT DOCUMENTS

| | | |
|---|---|---|
| WO | WO 2006/065648 | 6/2006 |
| WO | WO 2006/083515 | 8/2006 |
| WO | WO 2007/136459 | 11/2007 |
| WO | WO 2009/064583 | 5/2009 |

OTHER PUBLICATIONS

U.S. Appl. No. 61/305,987, filed Feb. 19, 2010, Kolb et al.
Cheng, H. N., "$^{13}C$ NMR Analysis of Ethylene-Propylene Rubbers," Macromolecules, vol. 17 (1984), pp. 1950-1955.
Ver Strate et al., "Near Monodisperse Ethylene-Propylene Copolymers by Direct Ziegler-Natta Polymerization," Macromolecules, vol. 21 (1988), pp. 3360-3371.
Wheeler et al., "Gel Permeation Chromatography/Fourier Transform Infrared Interface for Polymer Analysis," Applied Spectroscopy, vol. 47, No. 8 (1993), pp. 1128-1130.

* cited by examiner

*Primary Examiner* — Nathan M Nutter
(74) *Attorney, Agent, or Firm* — Jennifer A. Schmidt; Priya G. Prasad (57) ABSTRACT

Propylene-based polymer compositions are provided comprising propylene and from about 5 wt % to about 20 wt % of one or more $C_2$ and/or $C_4$-$C_{12}$ α-olefins. The polymer compositions have a triad tacticity greater than about 90%, a heat of fusion less than about 75 J/g, and a melt flow rate (MFR) greater than or equal to about 25 g/10 min (230° C., 2.16 kg). Further, the polymer compositions are reactor grade compositions comprising a reactor blend of a first polymer and a second polymer, preferably where both of the first and second polymers are prepared using the same catalyst system. Melt-spun nonwoven fabrics, such as meltblown or spunbond fabrics, comprising such polymer compositions are also provided, as well as processes for forming the nonwoven fabrics.

16 Claims, 3 Drawing Sheets

POLYMER COMPOSITIONS AND NONWOVEN COMPOSITIONS PREPARED THEREFROM

CROSS REFERENCE TO RELATED APPLICATIONS

This application is a divisional application of and claims priority to U.S. application Ser. No. 13/310,146, filed Dec. 2, 2011, the disclosure of which is incorporated herein by reference. This application is related to U.S. Ser. No. 61/411,708, filed Nov. 9, 2010; U.S. Ser. No. 13/015,364, filed Jan. 27, 2011; U.S. Ser. No. 12/271,526, filed Nov. 14, 2008; U.S. Ser. No. 61/101,341, filed Sep. 30, 2008; U.S. Ser. No. 61/157,524, filed Mar. 4, 2009; U.S. Ser. No. 12/566,564, filed Sep. 24, 2009; U.S. Ser. No. 61/156,078, filed Feb. 27, 2009; U.S. Ser. No. 12/566,410, filed Sep. 24, 2009; U.S. Ser. No. 61/171,135, filed Apr. 21, 2009; U.S. Ser. No. 12/566,434, filed Sep. 24, 2009; U.S. Ser. No. 61/248,254, filed Oct. 2, 2009; U.S. Ser. No. 12/894,955, filed Sep. 30, 2010; U.S. Ser. No. 12/723,317, filed Mar. 12, 2010; U.S. Ser. No. 12/723,336, filed Mar. 12, 2010; and U.S. Ser. No. 12/726,642, filed Mar. 18, 2010, each of which are herein incorporated by reference in their entireties.

BACKGROUND OF THE INVENTION

Propylene-based polymers and copolymers are well known in the art for their usefulness in a variety of applications, including the manufacture of nonwoven fabrics. Such fabrics have a wide variety of uses, such as in medical and hygiene products, clothing, filter media, and sorbent products. Meltblown nonwoven fabrics are particularly useful in hygiene products, such as baby diapers, adult incontinence products, and feminine hygiene products. An important aspect of these fabrics, particularly in hygiene applications, is the ability to produce aesthetically pleasing fabrics having good leakage performance at a low cost. Good leakage performance is achieved via the elasticity of the elastic layers of the fabrics, which provides better fit and conformity to the wearer, resulting in fewer leaks.

Production of meltblown nonwoven fabrics using commercially available propylene-based polymers having a melt flow rate (MFR) less than 25 g/10 min in the elastic layers can be difficult, because the low MFR of such polymers requires high melt temperatures and high pressures to melt blow. High process temperatures can cause undesirable degradation in the extruder, while high pressures limit the throughput rate of the melt blowing equipment. Previously, some propylene-based polymers have been blended with an additional polymer or polymers post-reactor, often isotactic propylene homopolymers, and then visbroken with peroxide to achieve a higher MFR polymer for use in elastic layers. Blending with an additional polymer, however, typically increases manufacturing cost and reduces the elastic performance of the resulting nonwoven fabrics. Similarly, visbreaking also increases manufacturing costs and adds complexity to manufacturing processes.

It is therefore desirable to form the elastic layers of meltblown nonwoven fabrics from propylene-based polymers having a higher MFR (i.e., greater than 25 g/10 min) without blending the propylene-based polymers post-reactor with homopolypropylene or other polymers and without visbreaking the polymers. Such fabrics can be produced under broader process conditions, and at higher throughput rates and lower costs.

U.S. Patent Application Publication No. 2002/0019507 describes propylene-based polymers that have been visbroken with peroxide to increase the MFR of the polymer for use in adhesive applications.

U.S. Patent Application Publication No. 2005/0130544 describes blends of propylene-based polymers with propylene homopolymers for use in fiber spinning applications.

U.S. Patent Application Publication No. 2008/0172840 describes polyolefin blend compositions suitable for use in spunbond fiber or filament applications having an MFR between 100 and 500 g/10 min.

U.S. Patent Application Publication No. 2009/0124154 describes nonwoven fabrics comprising two or more propylene-based elastomers and one or more propylene-based thermoplastic polymers.

International Publication No. WO 2009/064583 describes nonwoven fabrics made from compositions comprising a low crystallinity propylene-based elastomer, a high crystallinity propylene-based elastomer, and a propylene-based thermoplastic polymer.

SUMMARY OF THE INVENTION

The present invention is directed to polymer compositions, meltblown nonwoven compositions, and to processes for forming them. In one or more embodiments, the invention is directed to propylene-based polymer compositions comprising propylene and from about 5 wt % to about 20 wt % of one or more $C_2$ and/or $C_4$-$C_{12}$ α-olefins. The polymer compositions have a triad tacticity greater than about 90%, a heat of fusion less than about 75 J/g, and a melt flow rate (MFR) greater than or equal to about 25 g/10 min (230° C., 2.16 kg). Further, the polymer compositions are reactor grade compositions comprising a reactor blend of a first polymer and a second polymer, preferably where both of the first and second polymers are prepared using the same catalyst system. Preferably, the polymer composition has at least one of (a) a Die C tear strength greater than or equal to about 195 lbf/in (34,150 N/m), and (b) a force required to break apart two or more pellets formed from the polymer composition and stored under a load at 50° C. for one week of less than about 20 N.

The present invention is additionally directed to meltblown nonwoven fabrics having at least one elastic layer, wherein the elastic layer comprises a propylene-based polymer composition as described in the preceding paragraph. The present invention is also directed to processes for forming meltspun (e.g., meltblown or spunbond) nonwoven fabrics comprising forming a molten propylene-based polymer composition as previously described, forming fibers comprising the polymer composition, and forming an elastic nonwoven layer from the fibers.

DETAILED DESCRIPTION OF THE INVENTION

The invention is directed to propylene-based polymer compositions, meltspun nonwoven fabrics having at least one elastic layer comprising those propylene-based polymer compositions, and to processes for forming such fabrics. In certain embodiments, the propylene-based polymer composition comprises propylene and from about 5 wt % to about 20 wt % units derived from ethylene and/or a $C_4$-$C_{12}$ α-olefin. The propylene-based polymer compositions have a melt flow rate (MFR) greater than about 25 g/10 min, a heat of fusion (Hf) less than about 75 J/g, and a triad tacticity greater than about 90%. Further, the polymer compositions are reactor grade compositions comprising a reactor blend of a first polymer and a second polymer. In one or more embodiments, the first and second polymers are prepared using the same catalyst system.

As used herein, the term "copolymer" is meant to include polymers having two or more monomers, optionally with other monomers, and may refer to interpolymers, terpolymers, etc. The term "polymer" as used herein includes, but is not limited to, homopolymers, copolymers, terpolymers, etc., and alloys and blends thereof. The term "polymer" as used herein also includes impact, block, graft, random and alternating copolymers. The term "polymer" shall further include all possible geometrical configurations unless otherwise specifically stated. Such configurations may include isotactic, syndiotactic and random symmetries. The term "blend" as used herein refers to a mixture of two or more polymers.

The term "monomer" or "comonomer" as used herein can refer to the monomer used to form the polymer, i.e., the unreacted chemical compound in the form prior to polymerization, and can also refer to the monomer after it has been incorporated into the polymer, also referred to herein as a "[monomer]-derived unit", which by virtue of the polymerization reaction typically has fewer hydrogen atoms than it does prior to the polymerization reaction. Different monomers are discussed herein, including propylene monomers, ethylene monomers, and diene monomers.

"Polypropylene" as used herein includes homopolymers and copolymers of propylene or mixtures thereof. Products that include one or more propylene monomers polymerized with one or more additional monomers may be more commonly known as random copolymers (RCP) or impact copolymers (ICP). Impact copolymers are also known in the art as heterophasic copolymers. "Propylene-based," as used herein, is meant to include any polymer comprising propylene, either alone or in combination with one or more comonomers, in which propylene is the major component (i.e., greater than 50 wt % propylene).

"Reactor grade" as used herein means a polymer that has not been chemically or mechanically treated or blended after polymerization in an effort to alter the polymer's average molecular weight, molecular weight distribution, or viscosity. Particularly excluded from those polymers described as reactor grade are those that have been visbroken or otherwise treated or coated with peroxide. For the purposes of this disclosure, however, reactor grade polymers include those polymers that are reactor blends.

"Reactor blend" as used herein means a highly dispersed and mechanically inseparable blend of two or more polymers produced in situ as the result of sequential or parallel polymerization of one or more monomers with the formation of one polymer in the presence of another, or by solution blending polymers made separately in parallel reactors. Reactor blends may be produced in a single reactor, a series of reactors, or parallel reactors and are reactor grade blends. Reactor blends may be produced by any polymerization method, including batch, semi-continuous, or continuous systems. Particularly excluded from "reactor blend" polymers comprising a blend of two or more polymers in which the polymers are blended ex situ, such as by physically or mechanically blending in a mixer, extruder, or other similar device.

"Visbreaking" as used herein is a process for reducing the molecular weight of a polymer by subjecting the polymer to chain scission. The visbreaking process also increases the MFR of a polymer and may narrow its molecular weight distribution. Several different types of chemical reactions can be employed for visbreaking propylene-based polymers. An example is thermal pyrolysis, which is accomplished by exposing a polymer to high temperatures, e.g., in an extruder at 350° C. or higher. Other approaches are exposure to powerful oxidizing agents and exposure to ionizing radiation. The most commonly used method of visbreaking in commercial practice is the addition of a prodegradant to the polymer. A prodegradant is a substance that promotes chain scission when mixed with a polymer, which is then heated under extrusion conditions. Examples of prodegradants used in commercial practice are alkyl hydroperoxides and dialkyl peroxides. These materials, at elevated temperatures, initiate a free radical chain reaction resulting in scission of polypropylene molecules. The terms "prodegradant" and "visbreaking agent" are used interchangeably herein. Polymers that have undergone chain scission via a visbreaking process are said herein to be "visbroken." Such visbroken polymer grades, particularly polypropylene grades, are often referred to in the industry as "controlled rheology" or "CR" grades.

"Catalyst system" as used herein means the combination of one or more catalysts with one or more activators and, optionally, one or more support compositions. An "activator" is any compound or component, or combination of compounds or components, capable of enhancing the ability of one or more catalysts to polymerize monomers to polymers.

Propylene-Based Polymer Compositions

In one or more embodiments of the present invention, propylene-based reactor grade polymer compositions are provided comprising a reactor blend of a first polymer and a second polymer. The polymer compositions described herein are particularly suitable for use in the elastic layers of meltblown nonwoven fabrics, as well as in other applications.

In some embodiments, the propylene-based polymer compositions comprise propylene and from about 5 wt % to about 20 wt % of one or more comonomers selected from ethylene and/or $C_4$-$C_{12}$ α-olefins. In one or more embodiments, the α-olefin comonomer units may derive from ethylene, butene, pentene, hexene, 4-methyl-1-pentene, octene, or decene. The embodiments described below are discussed with reference to ethylene as the α-olefin comonomer, but the embodiments are equally applicable to other copolymers with other α-olefin comonomers. In this regard, the polymers may simply be referred to as propylene-based polymers or polymer compositions with reference to ethylene as the α-olefin.

In one or more embodiments, the propylene-based polymer compositions may include at least about 5 wt %, at least about 6 wt %, at least about 7 wt %, or at least about 8 wt %, or at least about 10 wt %, or at least about 12 wt % ethylene-derived units. In those or other embodiments, the polymers may include up to about 20 wt %, or up to about 19 wt %, or up to about 18 wt %, or up to about 17 wt % ethylene-derived units, or up to about 16 wt % ethylene-derived units, or up to about 15 wt % ethylene-derived units, where the percentage by weight is based upon the total weight of the propylene-derived and α-olefin derived units. In one or more embodiments, the propylene-based polymer compositions may desirably comprise from about 5 wt % to about 13 wt %, or from about 8 wt % to about 13 wt % ethylene-derived units. Stated another way, the propylene-based polymer compositions may include at least about 80 wt %, or at least about 81 wt % propylene-derived units, or at least about 82 wt % propylene-derived units, or at least about 83 wt % propylene-derived units, or at least about 84 wt % propylene-derived units, or at least about 85 wt % propylene-derived units; and in these or other embodiments, the polymers may include up to about 95 wt %, or up to about 94 wt %, or up to about 93 wt %, or up to about 92 wt %, or up to about 90 wt %, or up to about 88 wt % propylene-derived units, where the percentage by weight is based upon the total weight of the propylene-derived and alpha-olefin derived units.

The propylene-based polymer compositions contain a first and a second polymer. Thus, the comonomer content of the propylene-based polymer composition can be adjusted by adjusting the comonomer content of the first polymer, adjusting the comonomer content of second polymer, and/or adjusting the ratio of the first polymer to the second polymer present in the propylene-based polymer composition. Similarly, other properties described herein, such as MFR, of the propylene-based polymer composition can be adjusted by adjusting the property in the first polymer, adjusting the property in second polymer, and/or adjusting the ratio of the first polymer to the second polymer present in the propylene-based polymer composition, and so forth. In some embodiments, the first or second polymer is a random copolymer, preferably a random copolymer of propylene and ethylene, with the other polymer being a propylene-based elastomer.

The propylene-based polymer compositions of one or more embodiments are characterized by a melting point (Tm), which can be determined by differential scanning calorimetry (DSC). For purposes herein, the maximum of the highest temperature peak is considered to be the melting point of the polymer. A "peak" in this context is defined as a change in the general slope of the DSC curve (heat flow versus temperature) from positive to negative, forming a maximum without a shift in the baseline where the DSC curve is plotted so that an endothermic reaction would be shown with a positive peak.

In one or more embodiments, the Tm of the propylene-based polymer compositions (as determined by DSC) is less than about 115° C., or less than about 110° C., or less than about 100° C., or less than about 90° C.

In one or more embodiments, the propylene-based polymer compositions may be characterized by a heat of fusion (Hf), as determined by DSC. In one or more embodiments, the polymers may have an Hf that is at least about 0.5 J/g, or at least about 1.0 J/g, or at least about 1.5 J/g, or at least about 3.0 J/g, or at least about 4.0 J/g, or at least about 6.0 J/g, or at least about 7.0 J/g. In these or other embodiments, the polymers may be characterized by an Hf of less than about 75 J/g, or less than about 70 J/g, or less than about 60 J/g, or less than about 50 J/g, or less than about 30 J/g.

As used within this specification, DSC procedures for determining Tm and Hf include the following. The polymer is pressed at a temperature of from about 200° C. to about 230° C. in a heated press, and the resulting polymer sheet is hung, under ambient conditions, in the air to cool. About 6 to 10 mg of the polymer sheet is removed with a punch die. This 6 to 10 mg sample is annealed at room temperature for about 80 to 100 hours. At the end of this period, the sample is placed in a DSC (Perkin Elmer Pyris One Thermal Analysis System) and cooled to about −50° C. to about −70° C. The sample is heated at 10° C./min to attain a final temperature of about 200° C. The sample is kept at 200° C. for 5 minutes and a second cool-heat cycle is performed. Events from both cycles are recorded. The thermal output is recorded as the area under the melting peak of the sample, which typically occurs between about 0° C. and about 200° C. It is measured in Joules and is a measure of the Hf of the polymer.

The propylene-based polymer compositions can have a triad tacticity of three propylene units, as measured by $^{13}$C NMR, of 75% or greater, 80% or greater, 85% or greater, 90% or greater, 92% or greater, 95% or greater, or 97% or greater. In one or more embodiments, ranges include from about 75% to about 99%, in other embodiments from about 80% to about 99%, in other embodiments from about 85% to about 99%, in other embodiments from about 90% to about 99%, and in other embodiments from about 80% to about 97%. Triad tacticity is determined by the methods described in U.S. Patent Application Publication No. 2004/0236042.

The propylene-based polymer compositions may have a tacticity index m/r ranging from a lower limit of 4 or 6 to an upper limit of 8 or 10 or 12. The tacticity index, expressed herein as "m/r", is determined by $^{13}$C nuclear magnetic resonance ("NMR"). The tacticity index m/r is calculated as defined by H. N. Cheng in MACROMOLECULES, 1984, Vol. 17, pp. 1950-1955, incorporated herein by reference. The designation "m" or "r" describes the stereochemistry of pairs of contiguous propylene groups, "m" referring to meso and "r" to racemic. An m/r ratio of 1.0 generally describes a syndiotactic polymer, and an m/r ratio of 2.0 an atactic material. An isotactic material theoretically may have a ratio approaching infinity, and many by-product atactic polymers have sufficient isotactic content to result in ratios of greater than 50.

In one or more embodiments, the propylene-based polymer compositions may have a percent crystallinity of from about 0.5% to about 40%, or from about 1% to about 30%, or from about 5% to about 25%, determined according to DSC procedures. Crystallinity may be determined by dividing the $H_f$ of a sample by the $H_f$ of a 100% crystalline polymer, which is assumed to be 189 J/g for isotactic polypropylene or 350 J/g for polyethylene.

In one or more embodiments, the propylene-based polymer compositions may have a density of from about 0.85 g/cm$^3$ to about 0.92 g/cm$^3$, or from about 0.86 g/cm$^3$ to about 0.90 g/cm$^3$, or from about 0.86 g/cm$^3$ to about 0.89 g/cm$^3$ at room temperature as measured per the ASTM D-792 test method.

In one or more embodiments, the propylene-based polymer compositions can have a melt index (MI) (ASTM D-1238, 2.16 kg @ 190° C.), of greater than or equal to about 10 g/10 min, or greater than or equal to about 20 g/10 min, or greater than or equal to about 25 g/10 min, or greater than or equal to about 30 g/10 min.

In one or more embodiments, the propylene-based polymer compositions can have a melt flow rate (MFR), as measured according to ASTM D-1238, 2.16 kg weight @ 230° C., greater than about 25 g/10 min, or greater than about 27 g/10 min, or greater than about 29 g/10 min, or greater than about 30 g/10 min, or greater than about 40 g/10 min, or greater than about 50 g/10 min, or greater than about 60 g/10 min, or greater than about 70 g/10 min, or greater than about 80 g/10 min, or greater than about 90 g/10 min. In some embodiments, the propylene-based polymer compositions are reactor grade polymers having an MFR greater than about 25 g/10 min. In other words, the polymers have an MFR greater than 25 g/10 min as they are made in the reactor, and are not treated with peroxide or blended with another polymer to increase the MFR after exiting the reactor.

In one or more embodiments, the propylene-based polymer compositions may have a Mooney viscosity [ML (1+4) @ 125° C.], as determined according to ASTM D-1646, of less than about 100, or less than about 75, or less than about 50, or less than about 30.

In one or more embodiments, the propylene-based polymer compositions may have a g' index value of 0.95 or greater, or at least 0.97, or at least 0.99, wherein g' is measured at the Mw of the polymer using the intrinsic viscosity of isotactic polypropylene as the baseline. For use herein, the g' index is defined as:

$$g' = \frac{\eta_b}{\eta_l}$$

where $\eta_b$ is the intrinsic viscosity of the polymer and $\eta_l$ is the intrinsic viscosity of a linear polymer of the same viscosity-averaged molecular weight ($M_v$) as the polymer. $\eta_l = KM_v^\alpha$, K and α are measured values for linear polymers and should be obtained on the same instrument as the one used for the g' index measurement.

In one or more embodiments, the propylene-based polymer compositions can have a weight average molecular weight (Mw) of from about 5,000 to about 1,000,000 g/mole, or from about 10,000 to about 500,000 g/mole, or from about 20,000 to about 400,000 g/mole, or from about 50,000 to about 300,000 g/mole.

In one or more embodiments, the propylene-based polymer compositions can have a number average molecular weight (Mn) of from about 2,500 to about 2,500,000 g/mole, or from about 5,000 to about 500,000 g/mole, or from about 10,000 to about 250,000 g/mole, or from about 25,000 to about 200,000 g/mole.

In one or more embodiments, the propylene-based polymer compositions can have a Z-average molecular weight (Mz) of from about 10,000 to about 7,000,000 g/mole, or from about 50,000 to about 1,000,000 g/mole, or from about 80,000 to about 700,000 g/mole, or from about 100,000 to about 500,000 g/mole.

In one or more embodiments, the molecular weight distribution (MWD=(Mw/Mn)) of the propylene-based polymer compositions may be from about 1 to about 40, or from about 1 to about 15, or from about 1.8 to about 5, or from about 1.8 to about 3. In some embodiments of the invention, the propylene-based polymer compositions exhibit a bimodal molecular weight distribution.

Techniques for determining the molecular weight (Mn, Mw and Mz) and MWD may be found in U.S. Pat. No. 4,540,753 (Cozewith, Ju and Ver Strate) (which is incorporated by reference herein for purposes of U.S. practices) and references cited therein and in Macromolecules, 1988, Vol. 21, p. 3360-3371 (Ver Strate et al.), which is herein incorporated by reference for purposes of U.S. practices, and references cited therein. For example, molecular weight may be determined by size exclusion chromatography (SEC) by using a Waters 150 gel permeation chromatograph equipped with the differential refractive index detector and calibrated using polystyrene standards.

Optionally, the propylene-based polymer compositions may also include one or more dienes. The term "diene" is defined as a hydrocarbon compound that has two unsaturation sites, i.e., a compound having two double bonds connecting carbon atoms. Depending on the context, the term "diene" in this patent refers broadly to either a diene monomer prior to polymerization, e.g., forming part of the polymerization medium, or a diene monomer after polymerization has begun (also referred to as a diene monomer unit or a diene-derived unit). Exemplary dienes suitable for use in the present invention include, but are not limited to, butadiene, pentadiene, hexadiene (e.g., 1,4-hexadiene), heptadiene (e.g., 1,6-heptadiene), octadiene (e.g., 1,7-octadiene), nonadiene (e.g., 1,8-nonadiene), decadiene (e.g., 1,9-decadiene), undecadiene (e.g., 1,10-undecadiene), dodecadiene (e.g., 1,11-dodecadiene), tridecadiene (e.g., 1,12-tridecadiene), tetradecadiene (e.g., 1,13-tetradecadiene), pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, and polybutadienes having a molecular weight (Mw) of less than 1000 g/mol. Examples of straight chain acyclic dienes include, but are not limited to 1,4-hexadiene and 1,6-octadiene. Examples of branched chain acyclic dienes include, but are not limited to 5-methyl-1,4-hexadiene, 3,7-dimethyl-1,6-octadiene, and 3,7-dimethyl-1,7-octadiene. Examples of single ring alicyclic dienes include, but are not limited to 1,4-cyclohexadiene, 1,5-cyclooctadiene, and 1,7-cyclododecadiene. Examples of multi-ring alicyclic fused and bridged ring dienes include, but are not limited to tetrahydroindene; norbornadiene; methyltetrahydroindene; dicyclopentadiene; bicyclo(2.2.1)hepta-2,5-diene; and alkenyl-, alkylidene-, cycloalkenyl-, and cylcoalkylidene norbornenes [including, e.g., 5-methylene-2-norbornene, 5-ethylidene-2-norbornene, 5-propenyl-2-norbornene, 5-isopropylidene-2-norbornene, 5-(4-cyclopentenyl)-2-norbornene, 5-cyclohexylidene-2-norbornene, and 5-vinyl-2-norbornene]. Examples of cycloalkenyl-substituted alkenes include, but are not limited to vinyl cyclohexene, allyl cyclohexene, vinylcyclooctene, 4-vinylcyclohexene, allyl cyclodecene, vinylcyclododecene, and tetracyclododecadiene. In some embodiments of the present invention, the diene is selected from 5-ethylidene-2-norbornene (ENB); 1,4-hexadiene; 5-methylene-2-norbornene (MNB); 1,6-octadiene; 5-methyl-1,4-hexadiene; 3,7-dimethyl-1,6-octadiene; 1,3-cyclopentadiene; 1,4-cyclohexadiene; vinyl norbornene (VNB); dicyclopentadiene (DCPD), and combinations thereof. In one or more embodiments, the diene is ENB.

In some embodiments, the propylene-based polymer compositions comprise from 0.05 wt % to about 6 wt % diene-derived units. In further embodiments, the polymers comprise from about 0.1 wt % to about 5.0 wt % diene-derived units, or from about 0.25 wt % to about 3.0 wt % diene-derived units, or from about 0.5 wt % to about 1.5 wt % diene-derived units.

In certain embodiments, the propylene-based polymer compositions of the invention comprise a blend of a first polymer and a second polymer. The polymer compositions are reactor grade compositions, and the blend of the first and second polymers is a reactor blend. The first and second polymers may be the same or different, and each has a composition and properties as generally described above with respect to the overall blended propylene-based polymer compositions. Persons of skill in the art will recognize, however, that the compositions and properties of the first and second polymers comprising the blend may deviate from the ranges provided, so long as the resulting properties of the reactor blend compositions are as set forth herein. In certain embodiments of the invention, the first and second polymers are prepared using the same catalyst system.

Preparation of the Propylene-Based Polymer Compositions

As previously described, the propylene-based polymer compositions of the invention comprise a reactor blend of a first polymer and a second polymer. The first and second polymers are prepared with the same catalyst system, described in further detail below.

Polymerization of the propylene-based polymer compositions is conducted by reacting monomers in the presence of a catalyst system described herein typically at a temperature of from 0° C. to 200° C. for a time of from 1 second to 10 hours. Preferably homogeneous conditions are used, such as a continuous solution process or a bulk polymerization process with excess monomer used as diluent. The continuous process may use some form of agitation to reduce concentration differences in the reactor and maintain steady state polymerization conditions. The heat of the polymerization reaction is preferably removed by cooling of the polymerization feed and allowing the polymerization to heat up to the polymerization, although internal cooling systems may be used.

The polymers of the invention can be prepared with the catalyst systems described in batch, semi-continuous, or continuous propylene polymerization systems. Desirable polymerization systems are the continuous processes, including diluent slurry, bulk slurry (loop and stirred tank), solution process, and gas phase (stirred and fluid bed). Continuous polymerization can be carried out in a single reactor of any of the above types, in two or more reactors operating in series, or in two or more reactors operating in parallel. When two or more reactors are operating in a continuous process, the multiple reactors can be all of the same type or they may be any combination of the types.

Exemplary conditions suitable for preparation of the propylene-based polymer compositions described herein are illustrated below. Further details may be found in U.S. Pat. No. 6,881,800, which is incorporated by reference herein for purposes of U.S. practice.

|  | Reactor 1 | Reactor 2 | Product (Pellets) |
|---|---|---|---|
| Propylene-based polymer |  |  |  |
| Ethylene Content (wt. %) | 16 | 4 | 15 |
| MFR | 30 | 30 | 30 |
| Polysplit (wt. %) | 90% | 10% |  |
| Reactor |  |  |  |
| Polymerization Rate, kg/h | 9 | 1 |  |
| Conversions,($C_2=$/$C_3=$) wt. % | 73/40 | 60/30 |  |
| Reactor Attributes |  |  |  |
| Feed Temperature, degree C. | 5.0 | 5.0 |  |
| Reactor Temperatures, degree C. | 96.0 | 87.0 |  |
| Reactor Pressure, psig | 1600 | 1600 |  |

In one or more embodiments herein, the propylene-based polymer compositions are reactor blends comprising a first polymer and a second polymer. The polymer compositions may be produced by any reactor blend method currently known in the art. The polymers may be produced in any of the polymerization methods described above. The reactor blends may be produced in a single reactor, a series of reactors, or parallel reactors and are reactor grade blends. In some embodiments, substantially no additional homopolymers or copolymers of propylene are added to the compositions after the compositions exit the reactor.

The triad tacticity and tacticity index of the propylene-based polymer compositions may be controlled by the catalyst, which influences the stereoregularity of propylene placement, the polymerization temperature, according to which stereoregularity can be reduced by increasing the temperature, and by the type and amount of a comonomer, which tends to reduce the level of longer propylene derived sequences.

Too much comonomer may reduce the crystallinity provided by the crystallization of stereoregular propylene derived sequences to the point where the material lacks strength; too little and the material may be too crystalline. The comonomer content and sequence distribution of the polymers can be measured using $^{13}C$ nuclear magnetic resonance (NMR) by methods well known to those skilled in the art. Comonomer content of discrete molecular weight ranges can be measured using methods well known to those skilled in the art, including Fourier Transform Infrared Spectroscopy (FTIR) in conjunction with samples by GPC, as described in Wheeler and Willis, Applied Spectroscopy, 1993, Vol. 47, pp. 1128-1130. For a propylene ethylene copolymer containing greater than 75 wt % propylene, the comonomer content (ethylene content) of such a polymer can be measured as follows: A thin homogeneous film is pressed at a temperature of about 150° C. or greater, and mounted on a Perkin Elmer PE 1760 infrared spectrophotometer. A full spectrum of the sample from 600 cm−1 to 4000 cm−1 is recorded and the monomer weight percent of ethylene can be calculated according to the following equation: Ethylene wt %=82.585−111.987X+30.045X2, where X is the ratio of the peak height at 1155 cm−1 and peak height at either 722 cm−1 or 732 cm−1, whichever is higher. For propylene ethylene copolymers having 75 wt % or less propylene content, the comonomer (ethylene) content can be measured using the procedure described in Wheeler and Willis.

Reference is made to U.S. Pat. No. 6,525,157, whose test methods are also fully applicable for the various measurements referred to in this specification and claims and which contains more details on GPC measurements, the determination of ethylene content by NMR and the DSC measurements.

The catalyst may also control the stereoregularity in combination with the comonomer and the polymerization temperature. The propylene-based polymer compositions described herein are prepared using one or more catalyst systems. Catalyst systems suitable for use herein comprise at least a transition metal compound, also referred to as catalyst precursor, and an activator, and optionally a support composition. Contacting the transition metal compound (catalyst precursor) and the activator in solution upstream of the polymerization reactor or in the polymerization reactor of the disclosed processes yields the catalytically active component (catalyst) of the catalyst system. Any given transition metal compound or catalyst precursor can yield a catalytically active component (catalyst) with various activators, affording a wide array of catalysts deployable in the processes of the present invention. Catalyst systems of the present invention comprise at least one transition metal compound and at least one activator. Such catalyst systems may optionally include impurity scavengers. Each of these components is described in further detail below.

As used herein, prepared with the "same catalyst system" means that the referenced polymers are prepared using the same combination of a transition metal compound (catalyst precursor) and an activator. In other words, the "same catalyst system" requires only that the identity of the transition metal compound and activator combination be the same; it does not require, for example, that the same amounts of the transition metal compound (or the activator) be used to form the referenced polymers, nor does it require that the transition metal compound (or the activator) be used in the same polymerizing conditions to form the referenced polymers.

In one or more embodiments of the present invention, the catalyst systems used for producing the propylene-based polymer compositions comprise a metallocene compound. In some embodiments, the metallocene compound is a bridged bisindenyl metallocene having the general formula $(In^1)Y(In^2)MX_2$, where $In^1$ and $In^2$ are (preferably identical) substituted or unsubstituted indenyl groups bound to M and bridged by Y, Y is a bridging group in which the number of atoms in the direct chain connecting $In^1$ with $In^2$ is from 1 to 8 and the direct chain comprises C or Si, and M is a Group 3, 4, 5, or 6 transition metal. $In^1$ and $In^2$ may be substituted or unsubstituted. If $In^1$ and $In^2$ are substituted by one or more substituents, the substituents are selected from the group consisting of a halogen atom, $C_1$ to $C_{10}$ alkyl, $C_5$ to $C_{15}$ aryl, $C_6$ to $C_{25}$ alkylaryl, and N- or P-containing alkyl or aryl. Exemplary metallocene compounds of this type include, but are not limited to, µ-dimethyl-silylbis(indenyl)hafniumdimethyl and µ-dimethylsilylbis(indenyl)zirconiumdimethyl.

In other embodiments, the metallocene compound may be a bridged bisindenyl metallocene having the general formula $(In^1)Y(In^2)MX_2$, where $In^1$ and $In^2$ are identical 2,4-substituted indenyl groups bound to M and bridged by Y, Y is a bridging group in which the number of atoms in the direct chain connecting $In^1$ with $In^2$ is from 1 to 8 and the direct chain comprises C or Si, and M is a Group 3, 4, 5, or 6 transition metal. $In^1$ and $In^2$ are substituted in the 2 position by a methyl group and in the 4 position by a substituent selected from the group consisting of $C_5$ to $C_{15}$ aryl, $C_6$ to $C_{25}$ alkylaryl, and N- or P-containing alkyl or aryl. Exemplary metallocene compounds of this type include, but are not limited to, (µ-dimethyl-silyl)bis(2-methyl-4-(3',5'-di-tert-butylphenyl) indenyl)zirconiumdimethyl, (µ-dimethyl-silyl)bis(2-methyl-4-(3',5'-di-tert-butylphenyl)indenyl)hafniumdimethyl, (µ-dimethyl-silyl)bis(2-methyl-4-naphthylindenyl)zirconiumdimethyl, (µ-dimethylsilyl)bis(2-methyl-4-naphthylindenyl)hafniumdimethyl, (µ-dimethylsilyl)bis(2-methyl-4-(N-carbazyl)indenyl)-zirconiumdimethyl, and (µ-dimethylsilyl) bis(2-methyl-4-(N-carbazyl)indenyl)-hafniumdimethyl.

Alternatively, in one or more embodiments of the present invention, the metallocene compound may correspond to one or more of the formulas disclosed in U.S. Pat. No. 7,601,666. Such metallocene compounds include, but are not limited to, dimethylsilyl bis(2-(methyl)-5,5,8,8-tetramethyl-5,6,7,8-tetrahydrobenz(f)indenyl)hafnium dimethyl, diphenylsilyl bis(2-(methyl)-5,5,8,8-tetramethyl-5,6,7,8-tetrahydrobenz(f) indenyl)-hafnium dimethyl, diphenylsilyl bis(5,5,8,8-tetramethyl-5,6,7,8-tetrahydrobenz(f)indenyl)-hafnium dimethyl, diphenylsilyl bis(2-(methyl)-5,5,8,8-tetramethyl-5,6,7,8-tetrahydrobenz(f)indenyl)zirconium dichloride, and cyclo-propylsilyl bis(2-(methyl)-5,5,8,8-tetramethyl-5,6,7,8-tetrahydrobenz(f)indenyl)hafnium dimethyl.

In one or more embodiments of the present invention, the activators of the catalyst systems used to produce propylene-based polymer compositions comprise a cationic component. In some embodiments, the cationic component has the formula $[R^1R^2R^3AH]^+$, where A is nitrogen, $R^1$ and $R^2$ are together a —$(CH_2)_a$— group, where a is 3, 4, 5 or 6 and form, together with the nitrogen atom, a 4-, 5-, 6- or 7-membered non-aromatic ring to which, via adjacent ring carbon atoms, optionally one or more aromatic or heteroaromatic rings may be fused, and $R^3$ is $C_1$, $C_2$, $C_3$, $C_4$ or $C_5$ alkyl, or N-methylpyrrolidinium or N-methylpiperidinium. In other embodiments, the cationic component has the formula $[R_nAH]^+$, where A is nitrogen, n is 2 or 3, and all R are identical and are $C_1$ to $C_3$ alkyl groups, such as for example trimethylammonium, trimethylanilinium, triethylammonium, dimethylanilinium, or dimethylammonium.

In one or more embodiments of the present invention, the activators of the catalyst systems used to produce the propylene-based polymer compositions comprise an anionic component, $[Y]^-$. In some embodiments, the anionic component is a non-coordinating anion (NCA), having the formula $[B(R^4)_4]^-$, where $R^4$ is an aryl group or a substituted aryl group, of which the one or more substituents are identical or different and are selected from the group consisting of alkyl, aryl, a halogen atom, halogenated aryl, and haloalkylaryl groups. In one or more embodiments, the substituents are perhalogenated aryl groups, or perfluorinated aryl groups, including but not limited to perfluorophenyl, perfluoronaphthyl and perfluorobiphenyl.

Together, the cationic and anionic components of the catalysts systems described herein form an activator compound. In one or more embodiments of the present invention, the activator may be N,N-dimethylanilinium-tetra(perfluorophenyl)borate, N,N-dimethylanilinium-tetra(perfluoronaphthyl)borate, N,N-dimethylanilinium-tetrakis(perfluoro-biphenyl)borate, N,N-dimethylanilinium-tetrakis(3,5-bis (trifluoromethyl)phenyl)borate, triphenylcarbenium-tetra (perfluorophenyl)borate, triphenylcarbenium-tetra (perfluoro-naphthyl)borate, triphenylcarbenium-tetrakis (perfluorobiphenyl)borate, or triphenylcarbenium-tetrakis(3, 5-bis(trifluoromethyl)phenyl)borate.

Any catalyst system resulting from any combination of a metallocene compound, a cationic activator component, and an anionic activator component mentioned in the preceding paragraphs shall be considered to be explicitly disclosed herein and may be used in accordance with the present invention in the polymerization of one or more olefin monomers. Also, combinations of two different activators can be used with the same or different metallocene(s).

Suitable activators for the processes of the present invention also include alominoxanes (or alumoxanes) and aluminum alkyls. Without being bound by theory, an alumoxane is typically believed to be an oligomeric aluminum compound represented by the general formula $(R^x—Al—O)_n$, which is a cyclic compound, or $R^x(R^x—Al—O)_nAlR^2_2$, which is a linear compound. Most commonly, alumoxane is believed to be a mixture of the cyclic and linear compounds. In the general alumoxane formula, $R^x$ is independently a $C_1$-$C_{20}$ alkyl radical, for example, methyl, ethyl, propyl, butyl, pentyl, isomers thereof, and the like, and n is an integer from 1-50. In one or more embodiments, $R^x$ is methyl and n is at least 4. Methyl alumoxane (MAO), as well as modified MAO containing some higher alkyl groups to improve solubility, ethyl alumoxane, iso-butyl alumoxane, and the like are useful for the processes disclosed herein.

Further, the catalyst systems suitable for use in the present invention may contain, in addition to the transition metal compound and the activator described above, additional activators (co-activators) and/or scavengers. A co-activator is a compound capable of reacting with the transition metal complex, such that when used in combination with an activator, an active catalyst is formed. Co-activators include alumoxanes and aluminum alkyls.

In some embodiments of the invention, scavengers may be used to "clean" the reaction of any poisons that would otherwise react with the catalyst and deactivate it. Typical aluminum or boron alkyl components useful as scavengers are represented by the general formula $R^xJZ_2$ where J is aluminum or boron, $R^x$ is a $C_1$-$C_{20}$ alkyl radical, for example, methyl, ethyl, propyl, butyl, pentyl, and isomers thereof, and each Z is independently $R^x$ or a different univalent anionic ligand such as halogen (Cl, Br, I), alkoxide ($OR^x$) and the like. Exemplary aluminum alkyls include triethylaluminum, diethylaluminum chloride, ethylaluminum dichloride, tri-iso-butylaluminum, tri-n-octylaluminum, tri-n-hexylaluminum, trimethylaluminum and combinations thereof. Exemplary boron alkyls include triethylboron. Scavenging compounds may also be alumoxanes and modified alumoxanes including methylalumoxane and modified methylalumoxane.

In some embodiments, the catalyst system used to produce the propylene-based polymer compositions described herein includes a transition metal component which is a bridged bisindenyl metallocene having the general formula $(In^1)Y(In^2)MX_2$, where $In^1$ and $In^2$ are (preferably identical) substituted or unsubstituted indenyl groups bound to M and bridged by Y, Y is a bridging group in which the number of atoms in the direct chain connecting $In^1$ with $In^2$ is from 1 to 8 and the direct chain comprises C or Si, and M is a Group 3, 4, 5, or 6 transition metal. $In^1$ and $In^2$ may be substituted or unsubstituted. If $In^1$ and $In^2$ are substituted by one or more substituents, the substituents are selected from the group consisting of a halogen atom, $C_1$ to $C_{10}$ alkyl, $C_5$ to $C_{15}$ aryl, $C_6$ to $C_{25}$ alkylaryl, and N- or P-containing alkyl or aryl. In one or more embodiments, the transition metal component used to produce the propylene-based polymers is µ-dimethylsilylbis(indenyl)-hafniumdimethyl.

Properties of the Propylene-Based Polymer Compositions

The propylene-based polymer compositions of the present invention have mechanical properties and exhibit elastic performance making the polymers suitable for use in a variety of applications. For example, in one or more embodiments, the polymer compositions of the invention may have Shore A hardness values, determined in accordance with ASTM D-2240 (15 sec), greater than or equal to about 65, or greater than or equal to about 68, or greater than or equal to about 70, or greater than or equal to about 75. In the same or other embodiments, the compositions may have Vicat softening points, determined in accordance with ASTM D-1525 (200 g), greater than or equal to about 49° C., or greater than or equal to about 50° C., or greater than or equal to about 55° C., or greater than or equal to about 60° C.

Further, in some embodiments the polymer compositions may have a Die C tear strength, determined in accordance with ASTM D-624 greater than or equal to about 195 lbf/in (34150 N/m), or greater than or equal to about 200 lbf/in (35025 N/m), or greater than or equal to about 205 lbf/in (35901 N/m). The compositions may also have a flexural modulus (1% secant), determined in accordance with ASTM D-790, greater than or equal to about 1700 psi (11721 kPa), or greater than or equal to about 1800 psi (12411 kPa), or greater than or equal to about 2000 psi (13790 kPa), or greater than or equal to about 2500 psi (17237 kPa).

In some embodiments, the propylene-based polymer compositions of the present invention have good storage stability such that pellets comprising of the polymers exhibit little or no agglomeration (i.e., the pellets remain free-flowing) even when stored at elevated temperatures and/or under a load for extended periods of time. Alternatively, pellets comprising polymers of the invention may agglomerate, but require an amount of force less than about 30 N, or less than about 25 N, or less than about 20 N, or less than about 15 N to separate two or more of the pellets after they have been stored under a load at 50° C. for one week, indicating good storage stability. This storage stability test is performed using the following procedure: 35 grams of polymer pellets are placed into a 50 ml glass beaker having a diameter of about 40 mm. The bottom of the beaker is covered with a film of Teflon-coated woven glass fabric (Tygaflor, available commercially from Cammthane Pty Ltd) and the walls covered with a polyester film (Mylar, available commercially from DuPont Teijin Films) to avoid adhesion of the pellets to glass. The top layer of the pellets is also covered with a Tygaflor film. The beaker is then stored inside an air-ventilated oven at 50° C. for one week with a 1160 g weight applied on top of the pellets. At the end of one week, the beaker is removed from the oven and the sample allowed to cool to room temperature. If the sample is agglomerated or aggregated at the end of the storage, it is carefully removed from the beaker and placed (with the cylinder sections perpendicular) between the plates of a tensile machine operated in compression mode with a compression speed of 50 mm/min. At the end of the test, the force required to break the cylinder is reported. When pellets are free flowing at the end of the storage test, a zero force is reported.

Meltspun Nonwoven Compositions

In one or more embodiments, the present invention is directed to meltspun (e.g., meltblown or spunbond) nonwoven compositions (e.g. fabrics) comprising at least one elastic layer, wherein the elastic layer comprises a propylene-based polymer composition as described previously. As used herein "meltspun nonwoven composition" refers to a composition having at least one meltspun layer, and does not require that the entire composition be meltspun or nonwoven. In some embodiments, the nonwoven fabrics additionally comprise one or more facing layers positioned on one or both sides of the elastic layer(s). As used herein, "nonwoven" refers to a textile material that has been produced by methods other than weaving. For example, with nonwoven fabrics, the fibers may be processed directly into a planar sheet-like fabric structure and then are either bonded chemically, thermally, or interlocked mechanically (or both) to achieve a cohesive fabric.

The present invention is directed not only to nonwoven compositions such as fabrics, but also to processes for forming nonwoven compositions comprising the polymers described herein. In one or more embodiments, such methods comprise the steps of forming a molten polymer composition comprising a propylene-based polymer composition, forming fibers comprising the propylene-based polymer, and forming an elastic nonwoven layer from the fibers. In further embodiments, the process may further comprise the steps of forming one or more nonwoven facing layers, and disposing the elastic layer or layers upon the facing layer. Optionally, one or more facing layers may additionally be disposed upon the elastic layer or layers, such that the elastic layers are sandwiched between the facing layers.

Nonwoven fabrics of the present invention can be formed by any method known in the art. For example, the nonwoven fabrics may be produced by a meltblown or spunbond process. In certain embodiments herein, the elastic layer or layers of the fabrics of the invention are produced by a meltblown process. When the fabrics further comprise one or more facing layers, the facing layers may also be produced by a meltblown process, by a spunbond or spunlace process, or by any other suitable nonwoven process.

In one or more embodiments, the elastic layer or layers of the nonwoven fabrics described herein may be composed primarily of one or more propylene-based polymer compositions as described previously. While the elastic layers may comprise additives and/or fillers in addition to the propylene-based polymer compositions (which are reactor blends of a first polymer and a second polymer), no additional homopolymers or copolymers of propylene need to be blended with the propylene-based polymer compositions post-reactor to form the elastic layers. In other words, the elastic layers of the nonwoven fabrics can be substantially free of other propylene homopolymers and copolymers added post-reactor. While additional polymers may be blended, they are not required to achieve high MFR and good processability. This may result in improved meltblown nonwoven fabrics, because the post-reactor addition of other polymers, such as propylene homopolymers, increases the manufacturing cost and may reduce the elastic performance of the fabrics.

In the same or other embodiments, elastic layers formed from the propylene-based polymer compositions described herein may have $2^{nd}$ cycle permanent set values less than about 10%, or less than about 9.5%, or less than about 8.5%, or less than about 8%. In the same or other embodiments, such elastic layers may have $1^{st}$ cycle retractive force measurements (at 50% recovery), preferably at a basis weight of 75 gsm or less, of greater than about 1.3 N, greater than about 1.6 N, or greater than about 1.75 N, or greater than about 1.9 N, or greater than about 2.0 N, and $2^{nd}$ cycle retractive force measurements (at 50% recovery) greater than about 1.5 N, or greater than about 1.6 N, or greater than about 1.7 N, or greater than about 1.8 N, or greater than about 1.9 N, or greater than about 2.0 N.

Permanent set and retractive force at 50% recovery are determined as follows. Test samples measuring 50 mm×100 mm are stretched to 100% elongation at a speed of 500 mm/min. At 100% elongation, the samples are held for 1 second before being allowed to return to the starting position, also at a speed of 500 mm/min. The samples are held for 30 seconds, and the elongation cycle is repeated a second time. The test is conducted at 20° C. and 50% relative humidity. Permanent set is the increase in length, expressed as a percentage of the original length of the sample, by which the sample fails to return to its original length after each elongation cycle once the load is removed. For example, a permanent set of 0% means that after elongation the sample fully returns to its original length, while a permanent set of 100% means that the sample shows no elastic recovery at all after elongation. Retractive force at 50% recovery is the force exerted by a sample at 50% elongation, measured as the sample retracts from 100% elongation and expressed in N.

As used herein, "meltblown fibers" and "meltblown fabrics" refer to fibers formed by extruding a molten thermoplastic material at a certain processing temperature through a plurality of fine, usually circular, die capillaries as molten threads or filaments into high velocity, usually hot, gas streams which attenuate the filaments of molten thermoplastic material to reduce their diameter, which may be to microfiber diameter. Thereafter, the meltblown fibers are carried by the high velocity gas stream and are deposited on a collecting surface to form a web or nonwoven fabric of randomly dispersed meltblown fibers. Such a process is generally described in, for example, U.S. Pat. Nos. 3,849,241 and 6,268,302. Meltblown fibers are microfibers that are either continuous or discontinuous, and, depending on the resin, may be smaller than about 10 microns (for example, for high MFR isotactic polypropylene resins such as PP3746G or Achieve™ 6936G1, available from ExxonMobil Chemical Company); whereas for certain resins (for example, Vistamaxx™ propylene-based elastomer, available from ExxonMobil Chemical Company) or certain high throughput processes such as those described herein, meltblown fibers may have diameters greater than 10 microns, such as from about 10 to about 30 microns, or about 10 to about 15 microns. The term meltblowing as used herein is meant to encompass the meltspray process.

Commercial meltblown processes utilize extrusion systems having a relatively high throughput, in excess of 0.3 grams per hole per minute ("ghm"), or in excess of 0.4 ghm, or in excess of 0.5 ghm, or in excess of 0.6 ghm, or in excess of 0.7 ghm. The fabrics of the present invention may be produced using commercial meltblown processes, preferably a high pressure meltblown process available from Biax-Fiberfilm Corporation, or in test or pilot scale processes. In one or more embodiments of the present invention, the fibers used to form the nonwoven fabrics are formed using an extrusion system having a throughput rate of from about 0.01 to about 3.0 ghm, or from about 0.1 to about 2.0 ghm, or from about 0.3 to about 1.0 ghm.

In some embodiments, the fibers used to form the nonwoven fabrics are formed with an extrusion system producing a die pressure less than or equal to about 3000 psi (20684 kPa), or less than or equal to about 2500 psi (17237 kPa), or less than or equal to about 2000 psi (13790 kPa), or less than or equal to about 1750 psi (12066 kPa), or less than or equal to about 1500 psi (10342 kPa). In the same or other embodiments, the die pressure of the extrusion system may be greater than 100 psi (689 kPa), or greater than 250 psi (1724 kPa), or greater than 500 psi (3447 kPa), or greater than 750 psi (5171 kPa), or greater than 1000 psi (6895 kPa). In one or more embodiments of the invention, the die pressure is at least about 5%, or at least about 10%, or at least about 15% lower than that required to process a similar propylene-based polymer having the same ethylene content but having an MFR less than 25 g/10 min at the same throughput rate.

In the same or other embodiments, the extrusion system used to produce fibers according to the invention may be operated at a process temperature less than about 575° F. (302° C.), or less than about 570° F. (299° C.), or less than about 560° F. (293° C.), or less than about 550° F. (288° C.), or less than about 540° F. (282° C.).

In a typical spunbond process, polymer is supplied to a heated extruder to melt and homogenize the polymers. The extruder supplies melted polymer to a spinneret where the polymer is fiberized as passed through fine openings arranged in one or more rows in the spinneret, forming a curtain of filaments. The filaments are usually quenched with air at a low temperature, drawn, usually pneumatically, and deposited on a moving mat, belt or "forming wire" to form the nonwoven fabric. See, for example, in U.S. Pat. Nos. 4,340, 563; 3,692,618; 3,802,817; 3,338,992; 3,341,394; 3,502,763; and U.S. Pat. No. 3,542,615. The term spunbond as used herein is meant to include spunlace processes, in which the filaments are entangled to form a web using high-speed jets of water (known as "hydroentanglement").

The fibers produced in the spunbond process are usually in the range of from about 10 to about 50 microns in diameter, depending on process conditions and the desired end use for the fabrics to be produced from such fibers. For example, increasing the polymer molecular weight or decreasing the processing temperature results in larger diameter fibers. Changes in the quench air temperature and pneumatic draw pressure also have an affect on fiber diameter.

The fabrics described herein may be a single layer, or may be multilayer laminates. One application is to make a laminate (or "composite") from meltblown fabric ("M") and spunbond fabric ("S"), which combines the advantages of strength from spunbonded fabric and greater barrier properties of the meltblown fabric. A typical laminate or composite has three or more layers, a meltblown layer(s) sandwiched between two or more spunbonded layers, or "SMS" fabric composites. Examples of other combinations are SSMMSS, SMMS, and SMMSS composites. Composites can also be made of the meltblown or spunbond fabrics of the invention with other materials, either synthetic or natural, to produce useful articles.

In certain embodiments, the meltblown or spunbond nonwoven fabrics of the invention comprise one or more elastic layers comprising a propylene-based polymer composition as previously described and further comprise one or more facing layers positioned on one or both sides of the elastic layer(s). The facing layer or layers may comprise any material known in the art to be suitable for use in such layers. Examples of suitable facing layer materials include, but are not limited to, any available material typically used as a facing layer, such as polypropylene (PP), polyethylene (PE), polyethylene terephthalate (PET), polylactic acid (PLA), and polymer or fiber blends of two or more of the foregoing including bicomponent fibers such as those having a sheath-core structure.

A variety of additives may be incorporated into the polymer compositions used to make the fibers and fabrics described herein, depending upon the intended purpose. Such additives may include, but are not limited to, stabilizers, antioxidants, fillers, colorants, nucleating agents, dispersing agents, mold release agents, slip agents, fire retardants, plasticizers, pigments, vulcanizing or curative agents, vulcanizing or curative accelerators, cure retarders, processing aids, tackifying resins, and the like. Other additives may include fillers and/or reinforcing materials, such as carbon black, clay, talc, calcium carbonate, mica, silica, silicate, combinations thereof, and the like. Primary and secondary antioxidants include, for example, hindered phenols, hindered amines, and phosphates. Nucleating agents include, for example, sodium benzoate and talc. Also, to improve crystallization rates, other nucleating agents may also be employed such as Ziegler-Natta olefin products or other highly crystalline polymers. Other additives such as dispersing agents, for example, Acrowax C, can also be included. Slip agents include, for example, oleamide and erucamide. Catalyst deactivators are also commonly used, for example, calcium stearate, hydrotalcite, and calcium oxide, and/or other acid neutralizers known in the art.

The nonwoven products described above may be used in many articles such as hygiene products including, but not limited to, diapers, feminine care products, and adult incontinent products. The nonwoven products may also be used in medical products such as sterile wrap, isolation gowns, operating room gowns, surgical gowns, surgical drapes, first aid dressings, and other disposable items.

EXAMPLES

With reference to the following examples and figures, the following identifiers are used:

Polymer A is an inventive propylene-ethylene copolymer as described above, with an ethylene content of about 15 wt % and an MFR of about 29 g/10 min.

Polymer B is an inventive propylene-ethylene copolymer as described above, with an ethylene content of about 12 wt % and an MFR of about 30 g/10 min.

Comparative Polymer 1 is a propylene-ethylene copolymer having an ethylene content of about 15 wt % and an MFR of about 18 g/10 min. Comparative Polymer 2 is Comparative Polymer 1 visbroken with peroxide to an MFR of about 32 g/10 min.

Comparative Polymer 3 is a propylene-ethylene copolymer having an ethylene content of about 16 wt % and an MFR of about 3 g/10 min.

The following test methods were used to determine certain properties:

Melt Index ($I_2$ at 190° C.) and Melt Flow Rate ($I_2$ at 230° C.) were determined by ASTM D1238.

Hardness (15 sec) was determined by ASTM D2240.

Vicat Softening Point (200 g) was determined by ASTM D1525.

Flexural Modulus (1% secant) was determined by ASTM D790.

Tensile Strength at Break and Ultimate Elongation were determined by ASTM D638-99.

Tear Strength (Die C) was determined by ASTM D624.

In addition to the properties listed above, Top Load, Load Loss, and Permanent Set were also determined for plaques formed from Polymers A and B and Comparative Polymer 1. The results are reported in Table 1, below.

To prepare the polymer plaques, a 27.94 cm×27.94 cm plaque was formed by compression molding about 30 g of polymer between Teflon-coated sheets of aluminum foil at 200° C. for 15 minutes at a force of 25,000 kg. A brass frame having inner dimensions of 27.94 cm×27.94 cm and a thickness of 0.203 mm served as a spacer. After 15 minutes, the plaque was allowed to cool to room temperature while remaining under compression. The plaque was then removed from the frame and annealed for 48 hours at room temperature. Test specimens having the dimensions 76.2 mm×25.4 mm×0.203 mm were cut from the plaques and those test specimens were then used for hysteresis testing. The hysteresis testing was performed as follows.

Each test specimen was mounted on an Instron Renew 1130 tensile testing machine, available from Instron Corporation. The distance between the clamps was 25.4 mm. Each specimen was elongated to 200% of its original length, held at 200% elongation for 30 seconds, and relaxed to its original length. The specimen was then elongated to 200% elongation, held at 200% elongation for 30 seconds, and relaxed to its original length for a second time. Top Load is the load (in N) at 100% elongation during the first and second elongation, respectively. Load Loss is the difference between the load (in N) of the elongation and relaxation curves during the first and second relaxation cycles, respectively. Permanent set (in %) is the elongation at which the load on the sample is zero during the first and second relaxation cycles, respectively.

TABLE 1

| | Polymer A | Polymer B | Comparative Polymer 1 |
|---|---|---|---|
| Melt Index ($I_2$ @ 190° C.), g/10 min | 12 | 13 | 7 |
| Melt Flow Rate (12 @ 230° C.), g/10 min | 29 | 30 | 18 |
| Ethylene Content, wt % | 15 | 12 | 15 |
| Peak Melt Temperature (by DSC), ° C. | 97 | 100 | 104 |
| Heat of Fusion (1$^{st}$ melt), J/g | 11 | 21 | 11 |
| Density, g/cm3 | 0.863 | 0.870 | 0.863 |
| Hardness (15 sec), Shore A | 69 | 84 | 67 |
| Vicat Softening Point (200 g), ° C. | 51 | 63 | 49 |
| Flexural Modulus (1% Secant), psi | 1814 | 4970 | 1694 |
| Tensile Strength at Break, psi | no break | no break | no break |
| Ultimate Elongation, % | no break | no break | no break |
| Tear Strength (Die C), lbf/in | 207 | 289 | 188 |
| Hysteresis | | | |
| Load Loss (1$^{st}$ Cycle), N | 186 | 394 | 179 |
| Load Loss (2$^{nd}$ Cycle), N | 97 | 207 | 99 |
| Permanent Set (1$^{st}$ Cycle), % | 0.44 | 0.46 | 0.46 |
| Permanent Set (2$^{nd}$ Cycle), % | 0.40 | 0.42 | 0.40 |
| Top Load (100% 1$^{st}$ Cycle), N | 293 | 536 | 291 |
| Top Load (100% 2$^{nd}$ Cycle), N | 208 | 346 | 217 |

Polymers A and B and Comparative Polymers 1 and 2 were extruded in a 25 inch BIAX pilot line having 0.020" die capillaries at varying throughput rates and melt temperatures.

Figure 1:
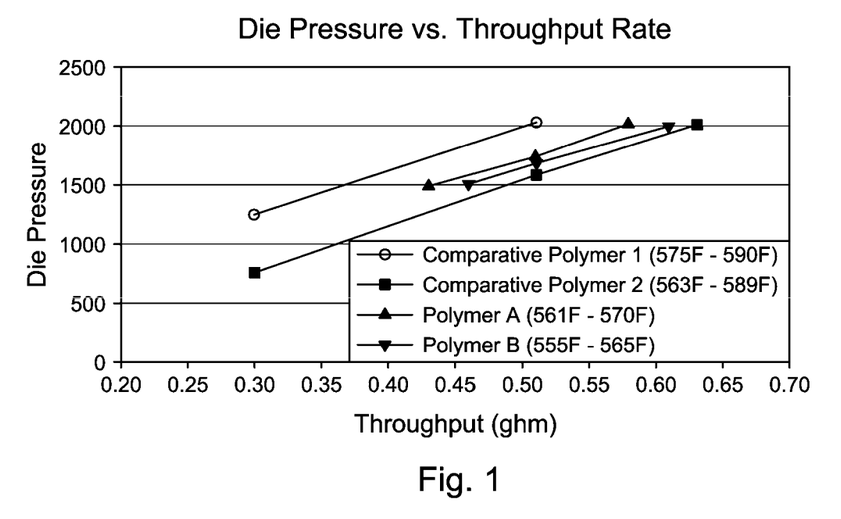
FIGS. 1 and 2 show die pressure versus throughput rate for the meltblown extrusion of comparative polymers and for polymers of the invention at various melt temperatures.

FIG. 1 depicts die pressure versus throughput rate for Polymers A and B, Comparative Polymer 1, and Comparative Polymer 2 at process temperatures between about 555° F. and 590° F. (291° C. and 310° C.). As shown in FIG. 1, the polymers of the invention could be run at lower die pressures than Comparative Polymer 1 while maintaining the same throughput levels. The inventive polymers were run at similar die pressures to Comparative Polymer 2 at the same throughput levels, but without requiring the added processing and expense of visbreaking with peroxide, which was required to achieve the performance exhibited by Comparative Polymer 2. Obtaining higher throughput rates at lower die pressures is desirable because it may allow higher production rates and improved profitability. In addition, the inventive polymers were able to be run at lower process temperatures than Comparative Polymer 1 as well.

Figure 2:
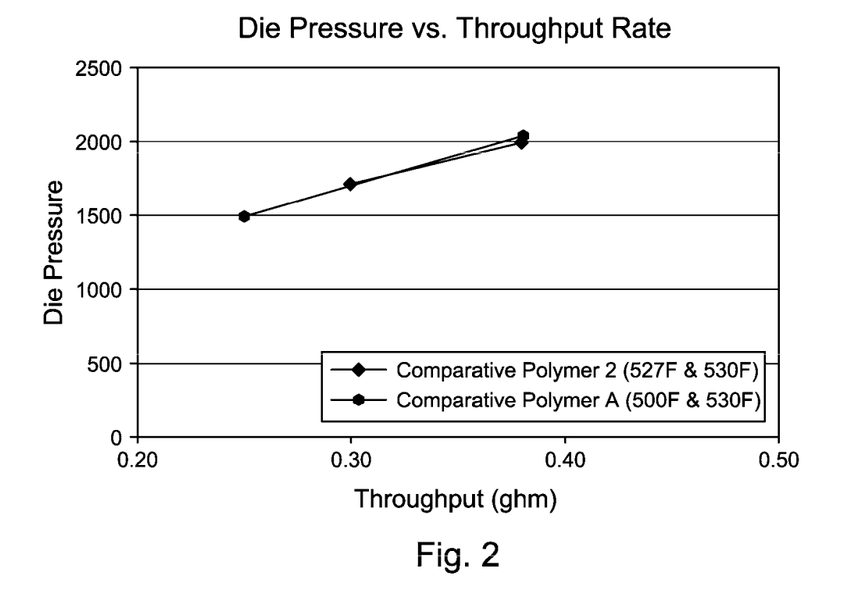

FIG. 2 depicts die pressure versus throughput rate for Polymer A and Comparative Polymer 2 at process temperatures between about 500° F. and 530° F. (260° C. and 277° C.). As shown in FIG. 2, inventive Polymer A could be run at similar die pressures to Comparative Polymer 2 at the same throughput levels, but without requiring the added processing and expense of visbreaking with peroxide, which was required to achieve the performance exhibited by Comparative Polymer 2. Additionally, the throughput rates of FIG. 2 are comparable to those depicted in FIG. 1, but are obtained at lower process temperatures. Elastomeric laminates were formed comprising center layers of Polymer A, Polymer B, or Comparative Polymer 1. All of the laminates further comprised facing layers on either side of the center layer formed from a 50/50 blend of homopolypropylene (PP) fibers and polyethylene terephthalate (PET) fibers commercially available from Jacob Holm.

Figure 3:
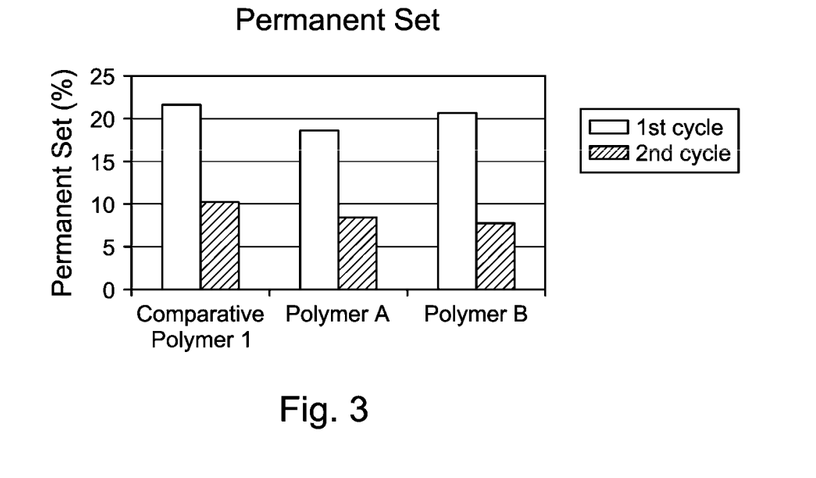
FIG. 3 shows permanent set measurements for polymers of the invention and a comparative polymer.

FIG. 3 depicts $1^{st}$ and $2^{nd}$ cycle permanent set results for such laminates comprising center layers of Comparative Polymer 1, Polymer A, and Polymer B. As shown in FIG. 3, improved (i.e., lower) permanent set results are achieved with the inventive polymers.

Figure 4:
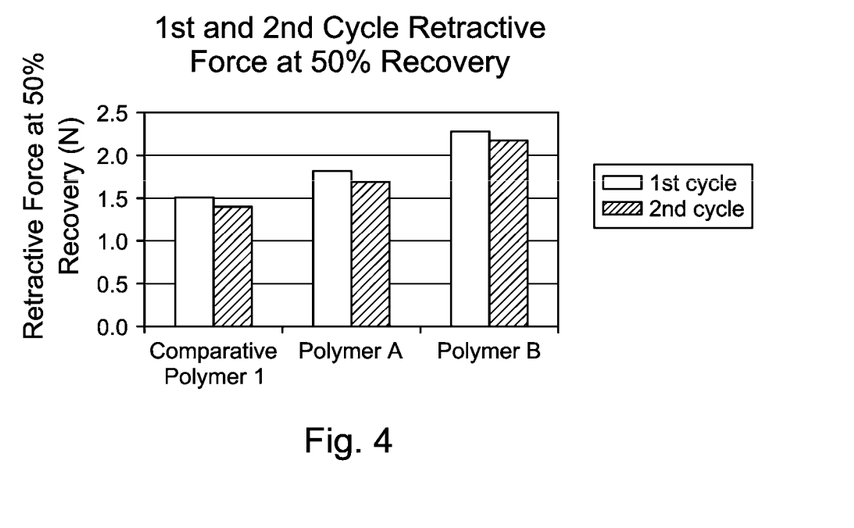
FIG. 4 shows retractive force measurements for polymers of the invention and a comparative polymer.

FIG. 4 depicts $1^{st}$ and $2^{nd}$ cycle retractive force at 50% recovery results for the same laminates. As shown in FIG. 4, the inventive polymers exhibit improved (i.e., higher) retractive force.

Figure 5:
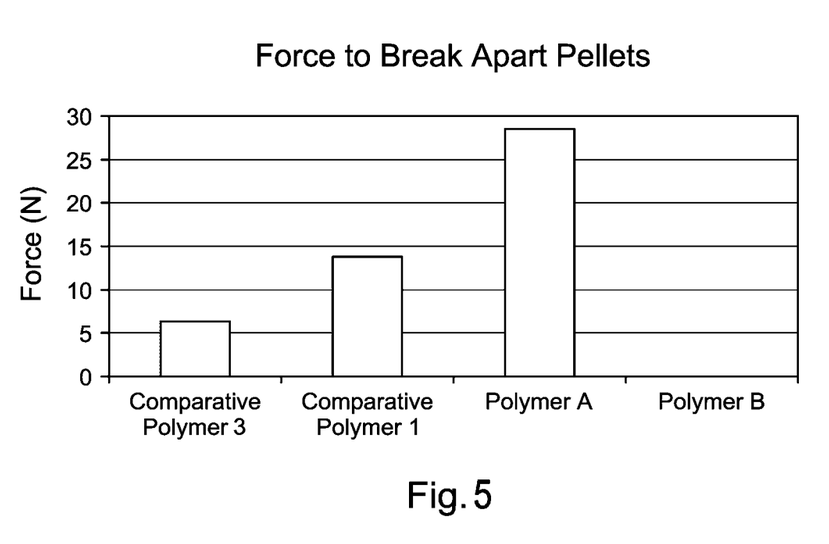
FIG. 5 shows storage stability testing results for polymers of the invention and comparative polymers.

FIG. 5 depicts the force required to break apart agglomerated pellets of Comparative Polymer 1, Comparative Polymer 3, Polymer A, and Polymer B using the storage stability test procedure described herein. As shown in FIG. 5, while the pellets of Polymer A agglomerated and required force to break apart, the pellets of Polymer B did not agglomerate even at elevated temperature and under a load and required no force to break apart. This is indicative of free flowing pellets, and therefore improved storage stability for pellets of inventive Polymer B.

For purposes of convenience, various specific test procedures are identified above for determining certain properties. However, when a person of ordinary skill reads this patent and wishes to determine whether a composition or polymer has a particular property identified in a claim, then any published or well-recognized method or test procedure can be followed to determine that property, although the specifically identified procedure is preferred. Each claim should be construed to cover the results of any of such procedures, even to the extent different procedures can yield different results or measurements. Thus, a person of ordinary skill in the art is to expect experimental variations in measured properties that are reflected in the claims.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

As used herein, the phrases "substantially no," and "substantially free of" are intended to mean that the subject item is not intentionally used or added in any amount, but may be present in very small amounts existing as impurities resulting from environmental or process conditions.

To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

Having described the various aspects of the compositions herein, further specific embodiments of the invention include those set forth in the following lettered paragraphs:

A. A propylene-based polymer composition comprising propylene and from about 5 wt % to about 20 wt % ethylene and/or a $C_4$-$C_{12}$ alpha-olefin, wherein the polymer composition has a triad tacticity greater than about 90%, a heat of fusion less than about 75 J/g, and an MFR greater than or equal to about 25 g/10 min (230° C., 2.16 kg);

the polymer composition is a reactor grade composition comprising a reactor blend of a first polymer and a second polymer; and the first and second polymers are prepared with the same catalyst system, preferably where the polymer composition has at least one of (a) a Die C tear strength greater than or equal to about 195 lbf/in, and (b) a force required to break apart two or more pellets formed from the polymer composition and stored under a load at 50° C. for one week of less than about 20 N.

B. The polymer composition of paragraph A, wherein the composition has an MFR greater than or equal to about 29 g/10 min.

C. The polymer composition of any of paragraphs A through B, wherein the composition comprises from about 5 wt % to about 13 wt % ethylene and/or a $C_4$-$C_{12}$ alpha-olefin.

D. The polymer composition of any of paragraphs A through C, wherein the composition has a melt temperature less than or equal to about 100° C.

E. The polymer composition of any of paragraphs A through D, wherein the composition has a Die C tear strength greater than or equal to about 195 lbf/in.

F. The polymer composition of any of paragraphs A through E, wherein the force required to break apart two or more pellets formed from the polymer composition and stored under a load at 50° C. for one week is less than about 20 N.

G. A meltspun nonwoven composition having at least one elastic layer, wherein the elastic layer comprises a propylene-based polymer composition, and wherein:

the polymer composition comprises propylene and from about 5 wt % to about 20 wt % ethylene and/or a $C_4$-$C_{12}$ alpha-olefin;

the polymer composition has a triad tacticity greater than about 90%, a heat of fusion less than about 75 J/g, and an MFR greater than or equal to about 25 g/10 min (230° C., 2.16 kg);

the polymer composition is a reactor grade composition comprising a reactor blend of a first polymer and a second polymer;

the first and second polymers are prepared with the same catalyst system; and the nonwoven composition has at least one of (a) a $2^{nd}$ cycle permanent set less than or equal to about 9%; (b) $1^{st}$ cycle retractive force at 50% recovery greater than about 1.6 N; and (c) a $2^{nd}$ cycle retractive force at 50% recovery greater than about 1.5 N.

H. The nonwoven composition of paragraph G, wherein the polymer composition has an MFR greater than or equal to about 29 g/10 min.

I. The nonwoven composition of any of paragraphs G through H, wherein the polymer composition comprises from about 5 wt % to about 13 wt % ethylene and/or a $C_4$-$C_{12}$ alpha-olefin.

J. The nonwoven composition of any of paragraphs G through I, wherein the nonwoven composition has a $2^{nd}$ cycle permanent set less than or equal to about 9%.

K. The nonwoven composition of any of paragraphs G through J, wherein the nonwoven composition has a $1^{st}$ cycle retractive force at 50% recovery greater than about 1.6 N, preferably at a basis weight of about 75 gsm or less.

L. The nonwoven composition of any of paragraphs G through K, wherein the nonwoven composition has a $2^{nd}$ cycle retractive force at 50% recovery greater than about 1.5 N, preferably at a basis weight of about 75 gsm or less.

M. The nonwoven composition of any of paragraphs G through L, further comprising one or more facing layers, preferably where the elastic layer is a meltblown layer, and at least one of the facing layers is a spunbond layer. Also preferably, the elastic layer is a meltblown layer positioned between two spunbond facing layers, and at least one of the spunbond layers comprises an impact copolymer.

N. The nonwoven composition of paragraph M, wherein the facing layer comprises polypropylene, polyethylene terephthalate, or a combination thereof.

O. An article comprising the nonwoven composition of any of paragraphs G through N.

P. The article of paragraph O, wherein the article is a diaper, adult incontinence product, or other personal hygiene product.

Q. A process for producing a meltspun, preferably meltblown or spunbond, composition, such as a nonwoven fabric, comprising:
  a. forming a molten propylene-based polymer composition comprising propylene and from about 5 wt % to about 20 wt % ethylene and/or a $C_4$-$C_{12}$ alpha-olefin and having a triad tacticity greater than about 90%, a heat of fusion less than about 75 J/g, and an MFR greater than or equal to about 25 g/10 min (230° C., 2.16 kg);
  b. forming fibers comprising the propylene-based polymer; and
  c. forming an elastic nonwoven fabric layer from the fibers; wherein
  the polymer composition is a reactor grade composition comprising a reactor blend of a first polymer and a second polymer, and the first and second polymers are prepared with the same catalyst system, and preferably wherein the meltspun composition has at least one of (a) a $2^{nd}$ cycle permanent set less than or equal to about 9%; (b) $1^{st}$ cycle retractive force at 50% recovery greater than about 1.6 N; and (c) a $2^{nd}$ cycle retractive force at 50% recovery greater than about 1.5 N.

R. The process of paragraph Q, wherein the polymer composition has an MFR greater than or equal to about 29 g/10 min.

S. The process of any of paragraphs Q through R, wherein the polymer composition comprises from about 5 wt % to about 13 wt % ethylene and/or a $C_4$-$C_{12}$ alpha-olefin.

T. The process of any of paragraphs Q through S, wherein the fibers are formed using an extrusion system having a die pressure less than or equal to about 2000 psi at a throughput rate of about 0.5 ghm.

U. The process of any of paragraphs Q through T, wherein the fibers are formed at a process temperature less than or equal to about 570° F.

V. The process of any of paragraphs Q through U, further comprising forming one or more nonwoven facing layers, and disposing the elastic nonwoven fabric layer upon the facing layer.

W. The process of paragraph V, wherein the facing layer comprises at least one of polypropylene and polyethylene terephthalate.

X. An article comprising an elastic nonwoven fabric layer formed by the process of any of paragraphs Q through W.

Y. The article of paragraph X, wherein the article is a diaper, adult incontinence product, or other personal hygiene product.

Z. A process for making a polymer composition, comprising the steps of:
  (a) preparing a first polymer in a first reactor using a first catalyst system;
  (b) preparing a second polymer in a second reactor using a second catalyst system;
  (c) combining the first polymer with the second polymer to form the polymer composition, wherein
  the first catalyst system and the second catalyst system are the same;
  the polymer composition is a reactor grade composition and comprises propylene and from about 5 wt % to about 20 wt % ethylene and/or a $C_4$-$C_{12}$ alpha-olefin, has a triad tacticity greater than about 90%, a heat of fusion less than about 75 J/g, and an MFR greater than or equal to about 25 g/10 min (230° C., 2.16 kg); and
  the polymer composition has at least one of (a) a Die C tear strength greater than or equal to about 195 lbf/in, and (b) a force required to break apart two or more pellets formed from the polymer composition and stored under a load at 50° C. for one week of less than about 20 N.

AA. The process of paragraph Z, wherein the polymer composition has an MFR greater than or equal to about 29 g/10 min.

AB. The process of paragraph any of paragraphs Z and AA, wherein the polymer composition comprises from about 5 wt % to about 13 wt % ethylene and/or a $C_4$-$C_{12}$ alpha-olefin.

AC. The process of any of paragraphs Z-AB, wherein the catalyst system comprises a transition metal compound that is a bridged bisindenyl metallocene having a formula (In$^1$)Y(In$^2$)MX$_2$, where In$^1$ and In$^2$ are (preferably identical) substituted or unsubstituted indenyl groups bound to M and bridged by Y, Y is a bridging group in which the number of atoms in the direct chain connecting In$^1$ with In$^2$ is from 1 to 8 and the direct chain comprises C or Si, and M is a Group 3, 4, 5, or 6 transition metal.

AD. The process of any of paragraphs Z-AC, wherein the catalyst system comprises a transition metal compound that is at least one of μ-dimethylsilylbis(indenyl)-hafniumdimethyl, μ-dimethylsilylbis(indenyl)zirconiumdimethyl, (μ-dimethylsilyl)bis(2-methyl-4-(3,'5'-di-tert-butylphenyl)indenyl)zirconiumdimethyl, (μ-dimethylsilyl)bis(2-methyl-4-(3,'5'-di-tert-butylphenyl)indenyl)hafniumdimethyl, (μ-dimethylsilyl)bis(2-methyl-4-naphthylindenyl)zirconiumdimethyl, (μ-dimethylsilyl)bis(2-methyl-4-naphthylindenyl)-hafniumdimethyl, (μ-dimethylsilyl)bis(2-methyl-4-(N-carbazyl)indenyl)zirconiumdimethyl, (μ-dimethylsilyl)bis(2-methyl-4-(N-carbazyl)indenyl)hafniumdimethyl, dimethylsilyl bis(2-(methyl)-5,5,8,8- tetramethyl-5,6,7,8-tetrahydrobenz(f)indenyl)hafnium dimethyl, diphenylsilyl bis(2-(methyl)-5,5,8,8-tetramethyl-5,6,7,8-tetrahydrobenz(f)indenyl)hafnium dimethyl, diphenylsilyl bis(5,5,8,8-tetramethyl-5,6,7,8-tetrahydrobenz(f)indenyl)hafnium dimethyl, diphenylsilyl bis(2-(methyl)-5,5,8,8-tetramethyl-5,6,7,8-tetrahydrobenz(f)indenyl)zirconium dichloride, and cyclo-propylsilyl bis(2-(methyl)-5,5,8,8-tetramethyl-5,6,7,8-tetrahydrobenz(f)indenyl)hafnium dimethyl.

AE. The process of any of paragraphs Z-AD, wherein the catalyst system comprises an activator that is at least one of N,N-dimethylanilinium-tetra(perfluorophenyl)borate, N,N-dimethylanilinium-tetra(perfluoronaphthyl)borate, N,N-dimethylanilinium-tetrakis(perfluorobiphenyl)borate, N,N-dimethylanilinium-tetrakis(3,5-bis(trifluoromethyl)phenyl)borate, triphenylcarbenium-tetra(perfluorophenyl)borate, triphenylcarbenium-tetra(perfluoronaphthyl)borate, triphenylcarbenium-tetrakis(perfluorobiphenyl)borate, triphenylcarbenium-tetrakis(3,5-bis(trifluoromethyl)-phenyl)borate, alominoxanes, alumoxanes, and aluminum alkyls.

While the foregoing is directed to embodiments of the present invention, other and further embodiments of the invention may be devised without departing from the basic scope thereof.

What we claim:

1. A nonwoven composition having at least one elastic layer, wherein the elastic layer comprises a propylene-based polymer composition, and wherein:

the polymer composition comprises propylene and from about 5 wt % to about 20 wt % ethylene and/or a $C_4$-$C_{12}$ alpha-olefin;

the polymer composition has a triad tacticity greater than about 90%, a heat of fusion less than about 75 J/g, and an MFR greater than or equal to about 25 g/10 min (230° C., 2.16 kg);

the polymer composition is a reactor grade composition comprising a reactor blend of a first polymer and a second polymer;

the first and second polymers are prepared with the same catalyst system; and the nonwoven composition has at least one of (a) a $2^{nd}$ cycle permanent set less than or equal to about 9%; (b) $1^{st}$ cycle retractive force at 50% recovery greater than about 1.6 N; and (c) a $2^{nd}$ cycle retractive force at 50% recovery greater than about 1.5 N.

2. The nonwoven composition of claim 1, wherein the polymer composition has an MFR greater than or equal to about 29 g/10 min.

3. The nonwoven composition of claim 1, wherein the polymer composition comprises from about 5 to about 13 wt % ethylene and/or a $C_4$-$C_{12}$ alpha-olefin.

4. The nonwoven composition of claim 1, wherein the nonwoven composition has a $2^{nd}$ cycle permanent set less than or equal to about 9%.

5. The nonwoven composition of claim 1, wherein the nonwoven composition has a $1^{st}$ cycle retractive force at 50% recovery greater than about 1.6 N.

6. The nonwoven composition of claim 1, wherein the nonwoven composition has a $2^{nd}$ cycle retractive force at 50% recovery greater than about 1.5 N.

7. The nonwoven composition of claim 1, further comprising one or more facing layers.

8. The nonwoven composition of claim 7, wherein the facing layer comprises at least one of polypropylene and polyethylene terephthalate.

9. The nonwoven composition of claim 7, wherein the elastic layer is a meltblown layer, and at least one of the facing layers is a spunbond layer.

10. The nonwoven composition of claim 7, wherein the elastic layer is a meltblown layer positioned between two spunbond facing layers, and wherein at least one of the spunbond layers comprises an impact copolymer.

11. An article comprising the nonwoven composition of claim 1.

12. The article of claim 11, wherein the article is a diaper, adult incontinence product, or other personal hygiene product.

13. The nonwoven composition of claim 1, wherein the polymer composition has at least one of (a) a Die C tear strength greater than or equal to about 195 lbf/in, and (b) a force required to break apart two or more pellets formed from the polymer composition and stored under a load at 50° C. for one week of less than about 20 N, based on the storage stability test.

14. The nonwoven composition of claim 1, wherein the polymer composition has a melt temperature less than or equal to about 100° C.

15. The nonwoven composition of claim 1, wherein the polymer composition has a Die C tear strength greater than or equal to about 195 lbf/in.

16. The nonwoven composition of claim 1, wherein the force required to break apart two or more pellets formed from the polymer composition and stored under a load at 50° C. for one week is less than about 20 N.

* * * * *